(12) United States Patent
Vogtherr

(10) Patent No.: US 12,096,953 B2
(45) Date of Patent: Sep. 24, 2024

(54) MEDICAL HAND-HELD INSTRUMENT COMPRISING A CLEANING-OPTIMIZED SPRING ELEMENT

(71) Applicant: AESCULAP AG, Tuttlingen (DE)

(72) Inventor: Robert Vogtherr, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 590 days.

(21) Appl. No.: 16/623,966

(22) PCT Filed: Jun. 27, 2018

(86) PCT No.: PCT/EP2018/067204
§ 371 (c)(1),
(2) Date: Dec. 18, 2019

(87) PCT Pub. No.: WO2019/002347
PCT Pub. Date: Jan. 3, 2019

(65) Prior Publication Data
US 2020/0138462 A1    May 7, 2020

(30) Foreign Application Priority Data
Jun. 27, 2017 (DE) .......................... 102017114260.6

(51) Int. Cl.
*A61B 17/28* (2006.01)
*A61B 17/3201* (2006.01)

(52) U.S. Cl.
CPC ...... *A61B 17/2841* (2013.01); *A61B 17/3201* (2013.01); *A61B 2017/2845* (2013.01)

(58) Field of Classification Search
CPC . A61B 17/2841; A61B 17/2909; A61B 17/30; A61B 17/3201; A61B 2017/2845;
(Continued)

(56) References Cited

U.S. PATENT DOCUMENTS 1,509,381 A * 9/1924 Townsend ............... A47L 17/04
15/210.1
3,521,510 A * 7/1970 Angquist ............... B26B 13/16
81/417
(Continued)

FOREIGN PATENT DOCUMENTS

DE        877357 C     5/1953
DE     69405253 T2    1/1998
(Continued)

OTHER PUBLICATIONS

German Search Report for German Application No. 10 2017 114 260.6, dated May 4, 2018, with English translation, 18 pages.
(Continued)

*Primary Examiner* — Sarah W Aleman
(74) *Attorney, Agent, or Firm* — Christopher A. Rothe; CM Law

(57) ABSTRACT

A medical hand-held instrument includes two handle elements that can swivel relative to one another, and a spring element having two spring element ends. The spring element ends are each connected to one of the two handle elements such that, when swiveling at least one of the two handle elements out of an initial position, a swiveling back into the initial position can be achieved by the spring element At least one of the two spring element ends is connected to the corresponding handle element via form-fit which is generated by reshaping the spring element. A method for producing a medical hand-held instrument includes connecting two handle elements such that they can swivel relative to each other.

14 Claims, 7 Drawing Sheets

(58) Field of Classification Search
CPC ...... A61B 2017/2919; A61B 2017/305; B25B 7/00; B25B 7/12
See application file for complete search history.

(56) References Cited

U.S. PATENT DOCUMENTS

| | | | | |
|---|---|---|---|---|
| 3,732,719 | A * | 5/1973 | Pallotta | A61B 17/2812 227/19 |
| 3,921,478 | A * | 11/1975 | Ygfors | B25B 7/00 81/417 |
| 3,990,137 | A * | 11/1976 | Kulba | B25B 27/205 81/352 |
| 4,793,224 | A * | 12/1988 | Huang | B25B 27/205 81/485 |
| 5,079,977 | A * | 1/1992 | Petrie | B25B 7/04 29/229 |
| 5,269,790 | A * | 12/1993 | Funatsu | A61B 17/128 606/205 |
| 5,470,328 | A | 11/1995 | Furnish et al. | |
| 5,782,749 | A | 7/1998 | Riza | |
| 6,071,299 | A * | 6/2000 | Dingler | A61B 17/2909 606/205 |
| 6,497,165 | B1 * | 12/2002 | Schulz | B25B 7/10 81/413 |
| 9,005,239 | B2 | 4/2015 | Seel | |
| 2003/0075026 | A1 | 4/2003 | Schulz et al. | |
| 2004/0087944 | A1 | 5/2004 | Hazebrouck | |
| 2010/0222800 | A1 | 9/2010 | Rebstock et al. | |
| 2011/0154958 | A1 * | 6/2011 | Wang | B25B 27/0071 81/302 |
| 2013/0323940 | A1 * | 12/2013 | Coffey | H01R 13/6205 385/139 |
| 2014/0041195 | A1 * | 2/2014 | Hoang | B25B 7/00 29/434 |
| 2014/0046363 | A1 * | 2/2014 | Frimand Ronnow | A61B 17/2841 606/205 |
| 2014/0296858 | A1 | 10/2014 | Seel | |
| 2016/0331396 | A1 * | 11/2016 | Schweitzer | A61B 17/2909 |
| 2016/0361079 | A1 | 12/2016 | Storz et al. | |

FOREIGN PATENT DOCUMENTS

| | | |
|---|---|---|
| DE | 10137915 A1 | 2/2003 |
| DE | 102007030874 A1 | 1/2009 |
| DE | 202009002433 U1 | 4/2009 |
| DE | 202009001809 U1 | 6/2009 |
| DE | 202010007995 U1 | 10/2010 |
| DE | 202011052256 U1 | 1/2012 |
| DE | 102011056235 A1 | 6/2013 |
| DE | 102014100603 A1 | 7/2015 |
| DE | 102014102606 A1 | 8/2015 |
| DE | 102014110881 A1 | 2/2016 |
| JP | 0531772 U | 4/1993 |
| WO | 9511112 A1 | 4/1995 |

OTHER PUBLICATIONS

International Search Report and Written Opinion for International Application PCT/EP2018/067204, dated Sep. 27, 2018, 11 pages.
Office Action received in Chinese Application No. 201880041712.4 dated Sep. 7, 2022, with translation, 20 pages.
Office Action received in Chinese Application No. 201880041712.4 dated Aug. 4, 2023, with translation, 14 pages.
Communication pursuant to Article 94(3) EPC received in Application No. 18 740 740.8-1113 dated Dec. 19, 2023, with translation, 12 pages.

* cited by examiner

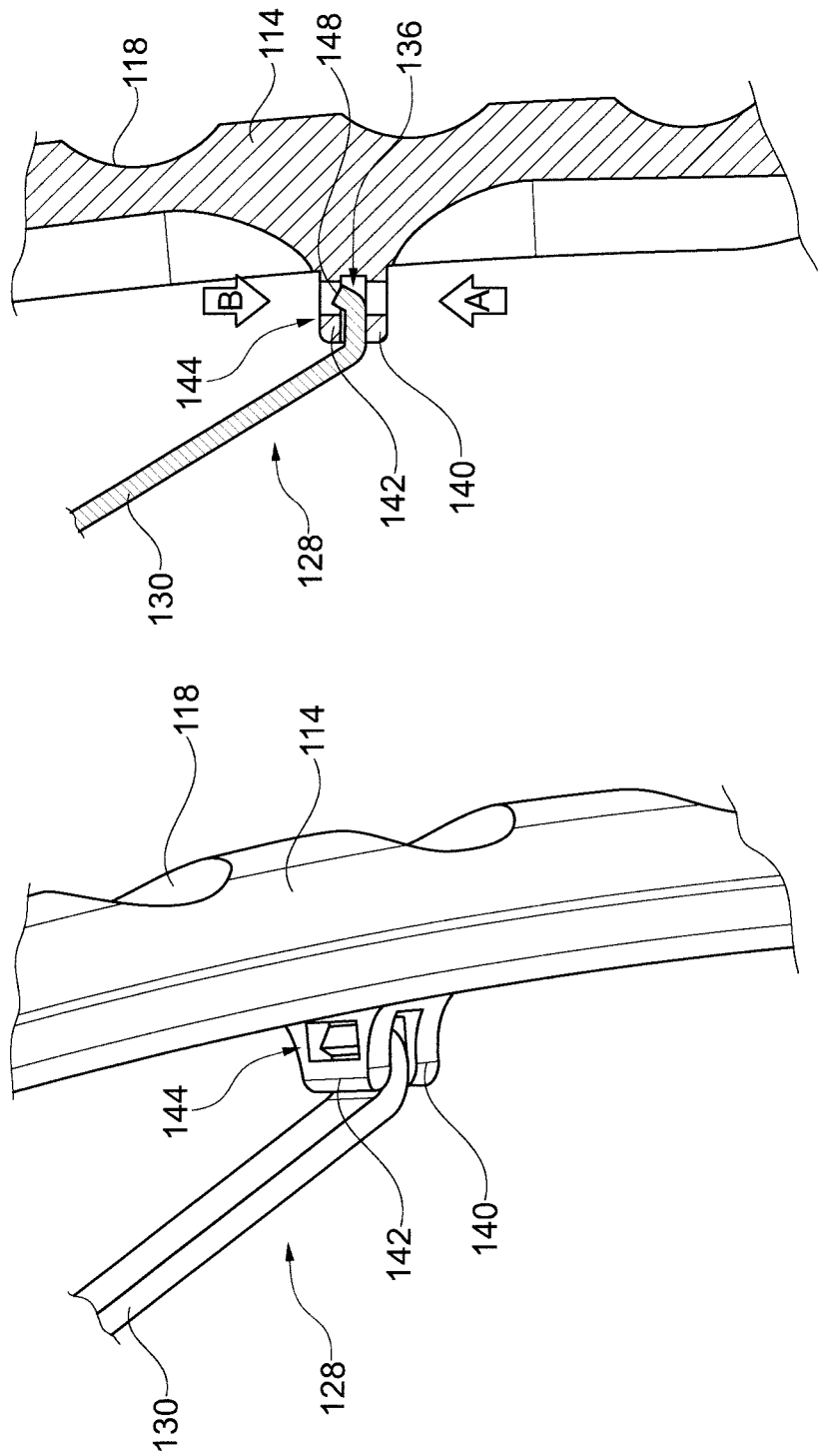

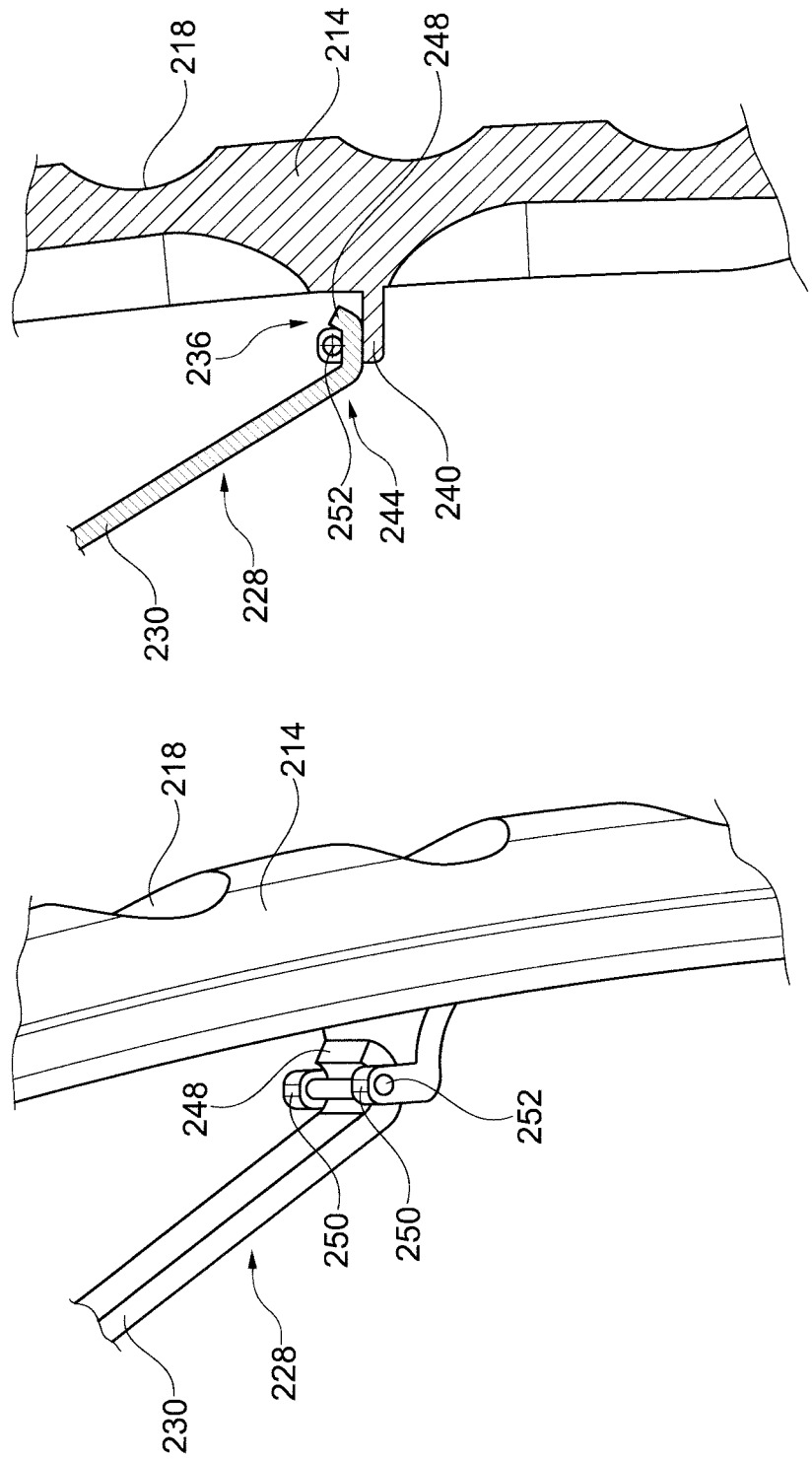

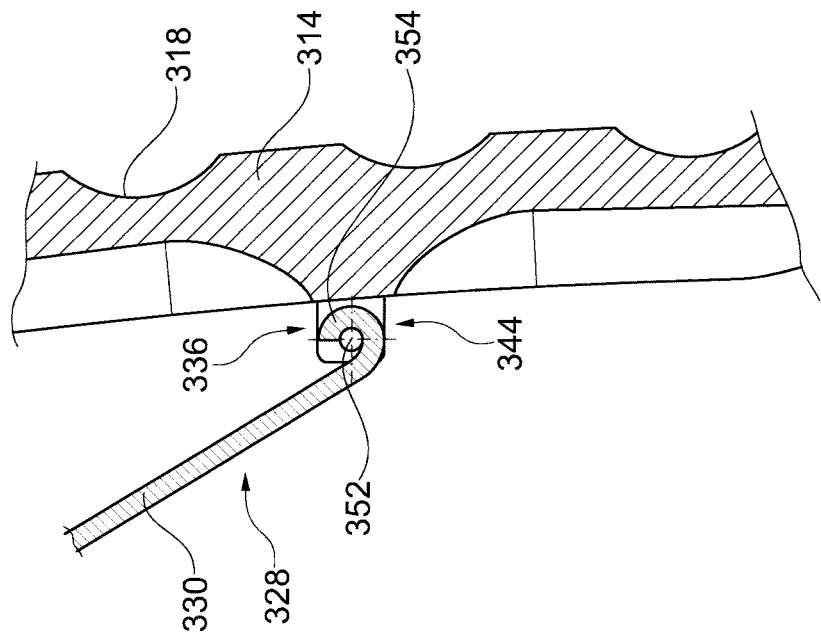
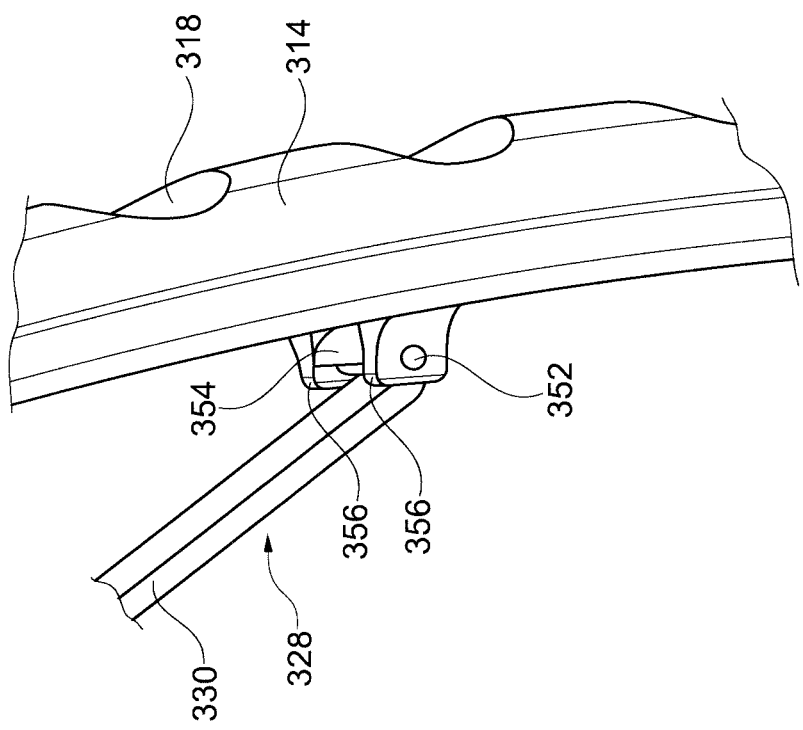

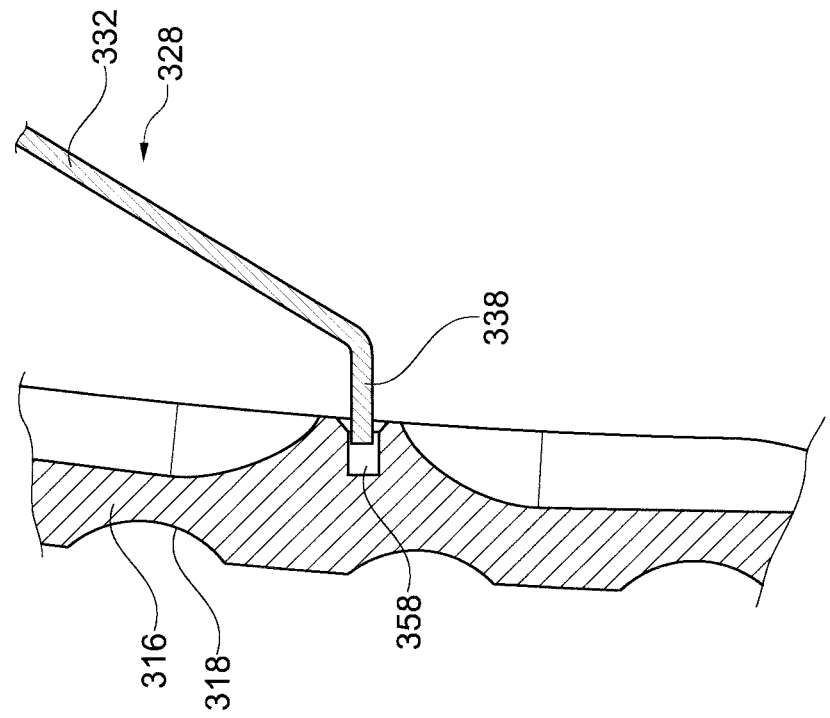
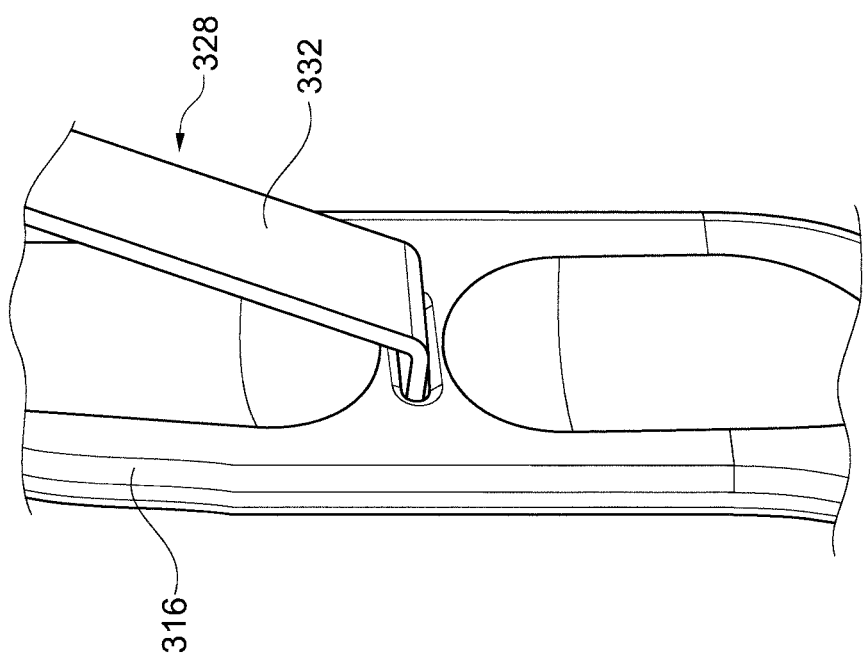

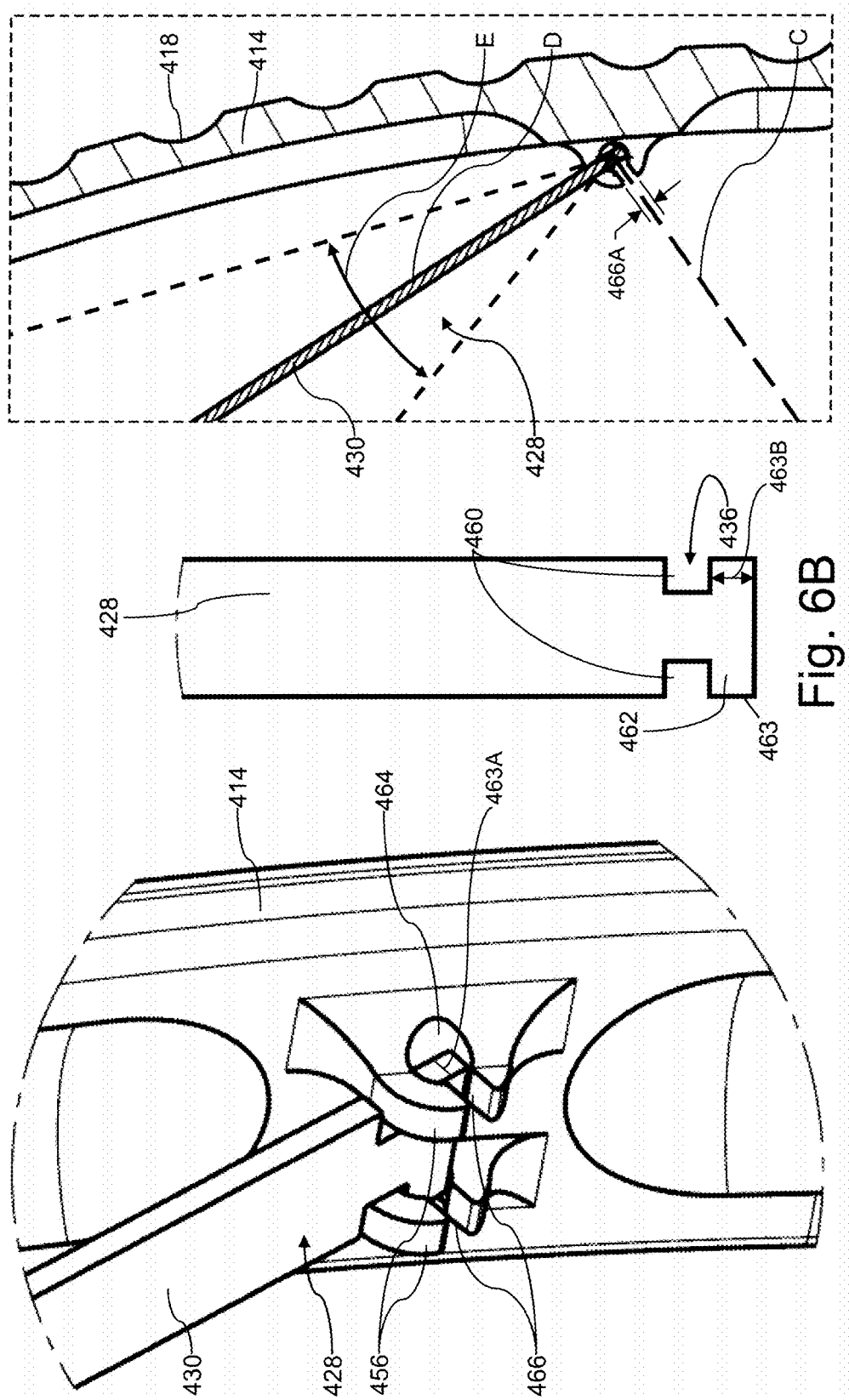

MEDICAL HAND-HELD INSTRUMENT COMPRISING A CLEANING-OPTIMIZED SPRING ELEMENT

CROSS REFERENCE TO RELATED APPLICATIONS

This application is the United States national phase entry of International Application No. PCT/EP2018/067204, filed Jun. 27, 2018, which claims the benefit of priority of German Application No. 10 2017 114 260.6, filed Jun. 27, 2017. The contents of International Application No. PCT/EP2018/067204 and German Application No. 10 2017 114 260.6 are incorporated by reference herein in their entireties.

FIELD

The present invention relates to a medical hand-held instrument, especially to a surgical hand-held instrument of the forceps or scissors type, comprising two handle elements or handle brackets that can swivel relative to each other, and a spring element, preferably a leaf spring that is bent in U or V shape, having two spring element ends each being connected to one of the two handle elements so that when swiveling at least one of the two handle elements out of an initial position, swiveling back into the initial position can be achieved by the spring element.

BACKGROUND

Publication DE 20 2010 007 995 U1 discloses an instrument in which a one-piece leaf spring is screwed on one side of the instrument or, resp., the instrument handle and with its free end abuts on the opposite side of the instrument or at the other instrument handle. This involves several drawbacks: In general, in surgical instruments threads should be avoided as far as possible, as the clearances between the nut thread and the screw practically cannot be cleaned. In the instrument according to publication DE 20 2010 007 995 U1, in the area of the screwed connection the leaf spring abuts directly on the inner face of the instrument, which also in this case results in a very narrow clearance between the leaf spring and the instrument that cannot be cleaned. Moisture or cleaning liquid can hardly dry out of said clearance and may have a corrosive effect over a certain period of time. In addition, the leaf spring is pierced in said area susceptible to corrosion and is weakened in its geometry, thus entailing a risk of breakage for the leaf spring at this position. In the support area on the opposite instrument side, the free leaf spring end causes friction during movement and, resp., use of the instrument. Said friction deteriorates the surface finish of the support area over time and equally increases the susceptibility to corrosion there.

Publication DE 20 2009 002 433 U1 discloses an instrument having two handles in which for each handle a screwed leaf spring member is provided. In order to cause swiveling back to an initial position, the two leaf spring members are supported against each other. As regards cleanability, the instrument according to the publication DE 20 2009 002 433 U1 shows the same drawbacks, especially due to its screw joints, as the instrument according to the publication DE 20 2010 007 995 U1. Furthermore, in the contact area of the two free leaf spring ends a plug connection that is relatively sharp-edged is provided. Since this position is located in the center of the easily accessible handle area of the instrument, the user's surgical glove may easily be cut or damaged. And even when said connecting point is properly deburred in the new state of the instrument, certain abrasion and burr will form after several applications.

Publication DE 20 2009 001 809 U1 relates to an instrument the spring mechanism of which consists of two screwed leaf spring members just as in the instrument according to publication DE 20 2009 002 433 U1. In order to avoid at least the afore-mentioned drawbacks of a sharp-edged plug connection point, a ball and socket geometry is provided between the leaf spring members. Because of the screw joints and the ball and socket geometry, the instrument according to DE 20 2009 001 809 U1 continues to be disadvantageous as regards its cleanability. Moreover, the manufacture of the spring mechanism according to DE 20 2009 001 809 U1 is complicated as the shown geometries have to be welded to the free leaf spring ends or have to be milled in a complex manner.

Publication DE 20 2011 052 256 U1 describes an instrument having a spring mechanism that consists of a screwed leaf spring member and a second member attached to be articulated to the free end thereof. Due to the screw joint and the complex design of the spring mechanism, also the instrument according to publication DE 20 2011 052 256 U1 is relatively difficult to clean and complicated to manufacture.

Instruments in which the spring mechanisms are formed at least partially integrally with corresponding handle parts in a complex manner are described, for example, in the publications DE 101 37 915 B4, DE 10 2007 030 874 B4 or DE 10 2014 102 606 A1. Said instruments show drawbacks not only due to their complex manufacture but also due to the poor exchangeability and removability of the leaf spring members.

SUMMARY

In view of the instruments according to the afore-mentioned prior art, it is the object of the present invention to provide a medical hand-held instrument which is easy to clean, shows relatively little wear and/or is relatively easy to repair and to produce.

The present invention therefore relates to a medical hand-held instrument comprising two handle elements (handle brackets, handle levers, lever arms) that can swivel relative to each other and a spring element (leaf spring). The spring element preferably bent in U or V shape has two ends which will be referred to as spring element ends below. Each of the two spring element ends is connected to the corresponding one of the two handle elements so that, when at least one of the two handle elements is swiveled out of an initial position relative to the other handle element, swiveling back into the initial position can be achieved by the spring element.

That is to say, when either of the two handle elements is manually swiveled by a user of the instrument, the spring element can swivel the swiveled handle element back into its initial position as soon as the user releases the swiveled handle part. Preferably, the medical hand-held instrument is a forceps-type or scissors-type instrument. Preferably, the hand-held instrument thus includes jaw elements or load arms opposed to a hinge which pivotally interconnects the handle elements. When the hand-held instrument is a forceps-type or scissors-type instrument, the initial position may refer to an open position or a closed position of the jaw elements. The medical hand-held instrument may be configured so that both handle elements are swiveled when the hand-held instrument is applied. The medical hand-held instrument may also be configured so that during use only one handle element is swiveled. If only one handle element is provided for being swiveled, the other handle element only serves as a counter-bearing for the user's hand during swiveling.

The medical hand-held instrument according to the invention excels by the fact that at least one of the two spring element ends is positively connected to the corresponding handle element via an undercut produced by plastically reshaping the spring element, and, in all positions of the spring element relative to the corresponding handle element, the undercut is engaged with said handle element such that dismounting is excluded.

The wording of "all positions of the spring element relative to the corresponding handle element" relates to all positions of the spring element which the spring element connected to the corresponding handle element can adopt relative to the corresponding handle element without the positive connection between the spring element and the corresponding handle element produced by plastic reshaping being destroyed.

In other words, at least one of the two spring element ends is or will be configured so that it can hook onto the corresponding handle element or can engage with the corresponding handle element. "Hooking" or "catching" or engaging", resp., in this context means that the connection between the spring element and the corresponding handle element is ensured at least in one direction by form-fit.

In accordance with the invention, said form-fit is achieved directly by reshaping the spring element rather than by means of auxiliary parts to be joined, such as rivets.

Reshaping may be carried out before, during or after attaching the spring element to the corresponding handle element. More exactly speaking, the separate sprint element thus initially can be plastically reshaped on at least one spring element end into a hook or an engaging structure and then can be caught or engaged with the corresponding handle element. It is also possible to attach or apply a spring element end which has not been reshaped to the corresponding handle element so as to catch or engage or connect said spring element end which is loosely attached or put against the handle element with the handle element by reshaping the spring element end. Ultimately, it is also possible that a spring element end, which already in advance has been configured in hook shape or engaging element shape in any possible manner, is threaded into a structure appropriately configured at the handle element for connection to the corresponding handle element. The spring element then is configured so that it is elastically reshaped at least temporarily during threading.

When, for connection of the spring element and the corresponding handle element, the spring element is reshaped, auxiliary parts to be joined can be advantageously dispensed with. Said omission of parts can be beneficial not only for the manufacture but also when cleaning the hand-held instrument according to the invention due to the reduced surface possibly resulting from the reduced number of components.

The cleanability and the producibility of the hand-held instrument can be further facilitated by integrally forming the spring element in accordance with an additional aspect of the invention. In particular, the spring element may be a leaf spring in U or V shape, thus having two legs. The two legs of the leaf spring can widen in the same direction as the two handle elements.

In order to improve the handling of the medical hand-held instrument, according to an additional aspect of the invention it can be advantageous to design the at least one spring element end caught with the corresponding handle element and/or the at least one handle element caught or engaged with the corresponding spring element end in such way that the spring element can be swiveled relative to the handle element in one swivel plane only. In other words, it may be of advantage to structurally design the catching or engagement of the spring element with the corresponding handle element such that at least in the initial position of the handle elements only one swivel movement of the spring element relative to the handle element, i.e. the swivel movement of the spring element in the swivel plane of the handle elements or in a plane in parallel to the swivel plane of the handle elements, is allowed. Swivel movements of the spring element in all other directions are then inhibited by the material of the handle element by form fit and/or friction fit.

When the at least one spring element end caught or engaged in the corresponding handle element is connected to the handle element by plastically reshaping the spring element, according to an additional aspect of the invention a relatively stable connection of the spring element end to the handle element can be ensured.

In accordance with an additional aspect of the invention, on the at least one handle element caught in the corresponding spring element end an eyelet in which the spring element end is caught may be provided. The eyelet may advantageously laterally enclose the hook-shaped or engaged spring element end so that inadvertent release of the connection between the hook-shaped or engaged spring element end and the corresponding handle element is less probable.

In accordance with an additional aspect of the invention, the eyelet can be formed by connecting two ends of a fork-shaped part of the corresponding handle element by means of a pin. This helps facilitate the manufacture of the hand-held instrument.

The production can also be facilitated, according to an additional aspect of the invention, by designing only one spring element end in hook shape or engaging element shape and designing a simpler connection of the other spring element end to the corresponding handle element. Concretely speaking, this means that the spring element end that is not hook-shaped and, resp., is not provided for engagement can be connected to the corresponding handle element merely by a plug connection. In the plug connection, the spring element end may protrude into a spring element end seat formed on the handle element and may be retained in the spring element end seat by canting. "Canting" in this context means that the spring force of the spring element rotates the corresponding spring element end within the spring element seat such that the spring element end is pressed locally, viz. at particular points, to inner walls of the spring element seat and at said points friction fit is created between the spring element end and the spring element seat. As an alternative, or in addition, also a connection of the spring element end which is not hook-shaped to the corresponding handle element can be achieved by means of press fit.

In accordance with an additional aspect of the invention, the at least one spring element end caught or engaged in the corresponding handle element may be connected to the handle element by elastic reshaping of the spring element. In this way, the connection between the hook-shaped or engaged spring element end and the corresponding handle element can be mounted and dismounted without using a tool, thus facilitating both the production and the cleaning of the hand-held instrument.

In accordance with an additional aspect of the invention, the at least one spring element end caught or engaged in the corresponding handle element may include two projections. For connecting the spring element to the corresponding handle element, bearing eyes with which the two protections can interact may be provided on the handle element. The two projections at the spring element end will hereinafter be referred to as spring element end projections. By providing two spring element end projections, the connection between the hook-shaped or engaged spring element end and the corresponding handle element can be better prevented from completely failing. If one spring element end projection is damaged such that it will no longer contribute to the connection between the spring element and the handle element, the other spring element end projection is capable of maintaining at least a provisional connection.

In accordance with an additional aspect of the invention, each of the two bearing eyes may include a slit extending in the axial direction of the bearing eye for inserting the respective spring element end projection. The slits may be dimensioned especially as parallel gaps so that the especially flatly configured spring element end projections can be inserted through the slits into the bearing eyes only when the spring element end equipped with the spring element end projections is aligned substantially in parallel to the slits. By means of the slits, the mounting and, resp., dismounting capability of the medical hand-held instrument can be further facilitated. When the slits are in the form of parallel gaps as afore-described, at the same time the safety of the connection can be ensured.

The present invention also relates to a method of manufacturing a medical hand-held instrument. The method comprises the following steps of:

connecting two handle elements (handle brackets, handle levers, lever arms) such that they can swivel relative to each other, forming a spring element (especially a leaf spring preferably in U or V shape) such that said spring element includes two spring element ends, plastic and/or elastic reshaping of the spring element and connecting each spring element end to the corresponding handle element such that, when swiveling at least one of the two handle elements out of an initial position, swiveling back into the initial position can be achieved by the spring element.

The method excels by the fact that reshaping of the spring element requires at least one of the two spring element ends to be positively connected to the corresponding handle element. According to the invention, at least one of the spring element ends is thus positively connected to the corresponding handle element by the fact that the spring element is plastically and/or elastically reshaped.

The positive connection can be made simultaneously with or after reshaping of the spring element.

In particular, simultaneously with reshaping of the spring element both spring element ends can be positively connected to the respective handle elements.

BRIEF DESCRIPTION OF THE DRAWING FIGURES

In the following, the present invention will be described in detail by way of preferred example embodiments with reference to the enclosed drawings, wherein:

FIG. 3A shows a perspective view of a catching of a spring element end with a handle element according to the invention as set forth in a second embodiment;

FIG. 3B shows a cross-sectional view of the catching shown in FIG. 3A;

FIG. 4A shows a perspective view of a catching of a spring element end with a handle element according to the invention as set forth in a third embodiment;

FIG. 4B shows a cross-sectional view of the catching shown in FIG. 4A;

FIG. 5A shows a perspective view of a catching of a spring element end with a handle element according to the invention as set forth in a fourth embodiment;

FIG. 5B shows a cross-sectional view of the catching shown in FIG. 5A;

FIG. 5C shows a perspective view of a spring element end inserted in a handle element as set forth in the fourth embodiment;

FIG. 5D shows a cross-sectional view of the spring element end illustrated in FIG. 5C;

FIG. 6A shows a perspective view of a catching of a spring element end with a handle element according to the invention as set forth in a fifth embodiment;

FIG. 6B shows a top view of the spring element end according to the fifth embodiment; and FIG. 6C shows a cross-sectional view of the catching illustrated in FIG. 6A.

Figure 1:
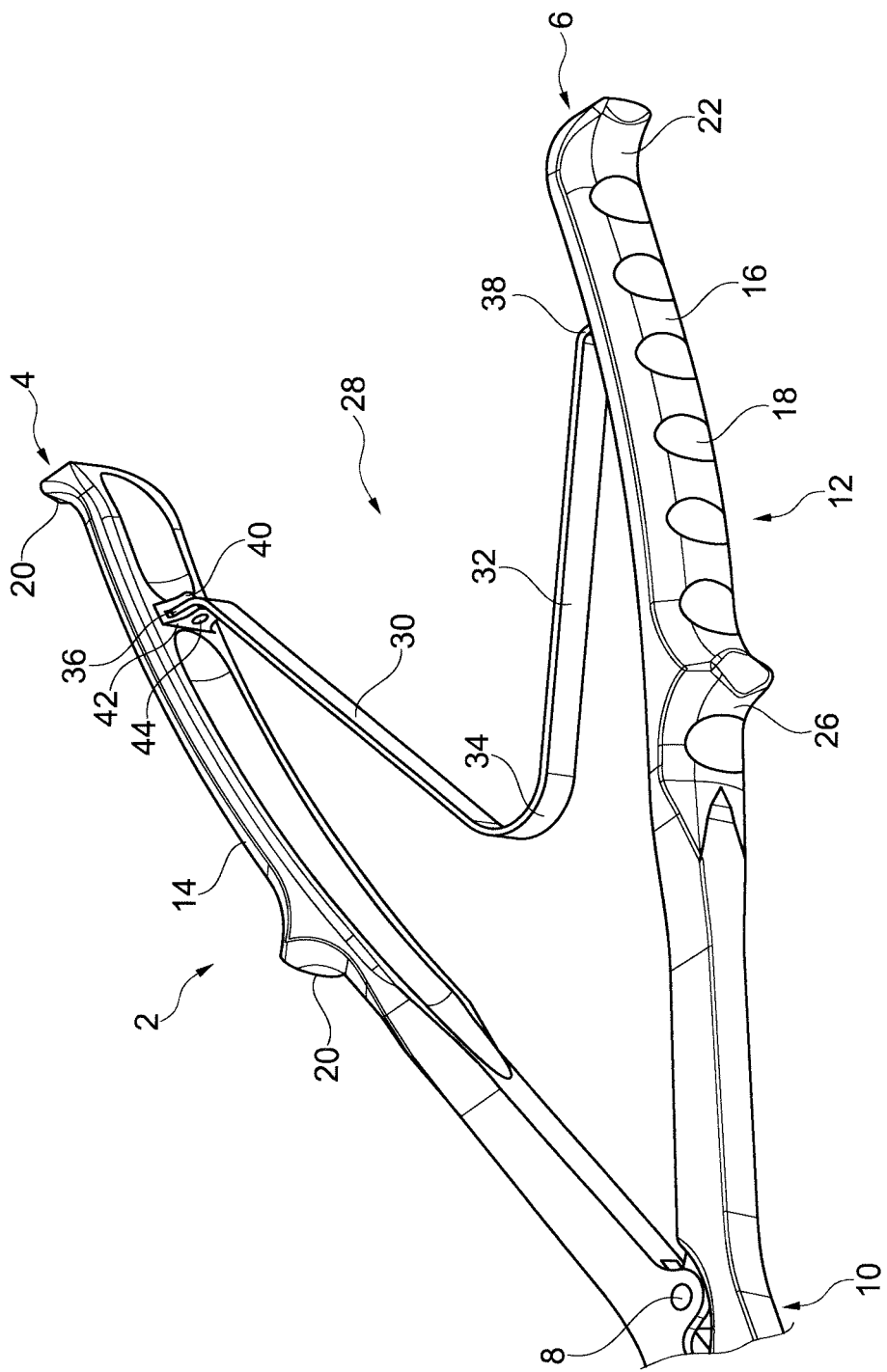
FIG. 1 shows a perspective detail view of a medical hand-held instrument according to the invention as set forth in a first embodiment.

Like or functionally equivalent features are provided with like reference numerals in the individual figures. Double-digit reference numerals relate to the first embodiment. Triple-digit reference numerals starting with the figure "1" relate to the second embodiment. Triple-digit reference numerals starting with the figure "2" relate to the third embodiment. Triple-digit reference numerals starting with the figure "3" relate to the fourth embodiment. Triple-digit reference numerals starting with the figure "4" relate to the fifth embodiment.

DETAILED DESCRIPTION

FIG. 1 illustrates a medical hand-held instrument 2 according to a first embodiment. The hand-held instrument 2 is a forceps or scissors design. That is to say, it includes two levers 4 and 6 which are pivoted to each other via a hinge 8. The portion of the hand-held instrument 2, on the one hand, of the hinge 8 is a jaw portion 10 (shown rudimentarily only). The portion, on the one hand, of the hinge 8 is a handle portion 12. The proximal parts of the levers 4 and 6 forming the handle portion 12 of the hand-held instrument 2 will be referred to as handle elements 14 and 16 in the following.

The handle element 14 of the lever 4 and the handle element 16 of the lever 6 are configured substantially symmetrically to each other. Each of the handle elements 14 and 16 has recesses 18 on the side facing away from the respective other handle element 16 and 14 to ensure proper feel when seizing the hand-held instrument 2. On the proximal side of the handle portion 12, at the free ends of the handle elements 14 and 16, the handle elements 14 and 16 include handle projections 20 and 22 on the side facing away from the respective other handle element 16 and 14. Also, hands away from each of the free ends the handle elements 14 and 16 include handle projections 24 and 26 on the side facing away from the respective other handle element 16 and 14. Each of the handle projections 20 and 24 and, resp., 22 and 26 restricts an area at the handle elements 14 and 16 at which a user preferably seizes or preferably is intended to seize the handle portion 12. The handle projections 20 and 24 and, resp., 22 and 26 are determined for preventing the user's fingers from sliding off Between the handle elements 4 and 6 a spring element 28 is provided. The spring element 28 is substantially U or V shaped and includes two legs 30 and 32 which are interconnected via a curved portion 34. At the respective free end thereof, the legs 30 and, resp., 32 are bent in the direction away from the respective other leg 32 and, resp., 30. Said bent areas will be referred to as connecting portions 36 and 38 in the following.

The two legs 30 and 32 as well as the curved portion 34 and the connecting portions 36 and 38 are formed integrally in the form of a bent leaf spring preferably made from spring steel.

The handle elements 14 and 16 include, on the respective side facing the respective other handle element 16 and, resp., 14, about two fingers away from the free end of the handle element 14 and 16, resp., two connecting plates 40 and 42 extending in parallel to each other and in parallel to the swivel axis of the hinge 8. Each of the two connecting plates 40 and 42 of a handle element 14 and, resp., 16 in the center has a cutout 44. The two connecting plates 40 and 42 of a respective handle element 14 and, resp., 16 are at such a distance from each other and, resp., the gap between the two connecting plates 40 and 42 of a respective handle element 14 and, resp., 16 is dimensioned such that, when mounting the spring element 28 to the handle elements 14 and 16, the connecting portions 36 and 38 can be inserted between the respective connecting plates 40 and 42 each with transition fit.

Figure 2:
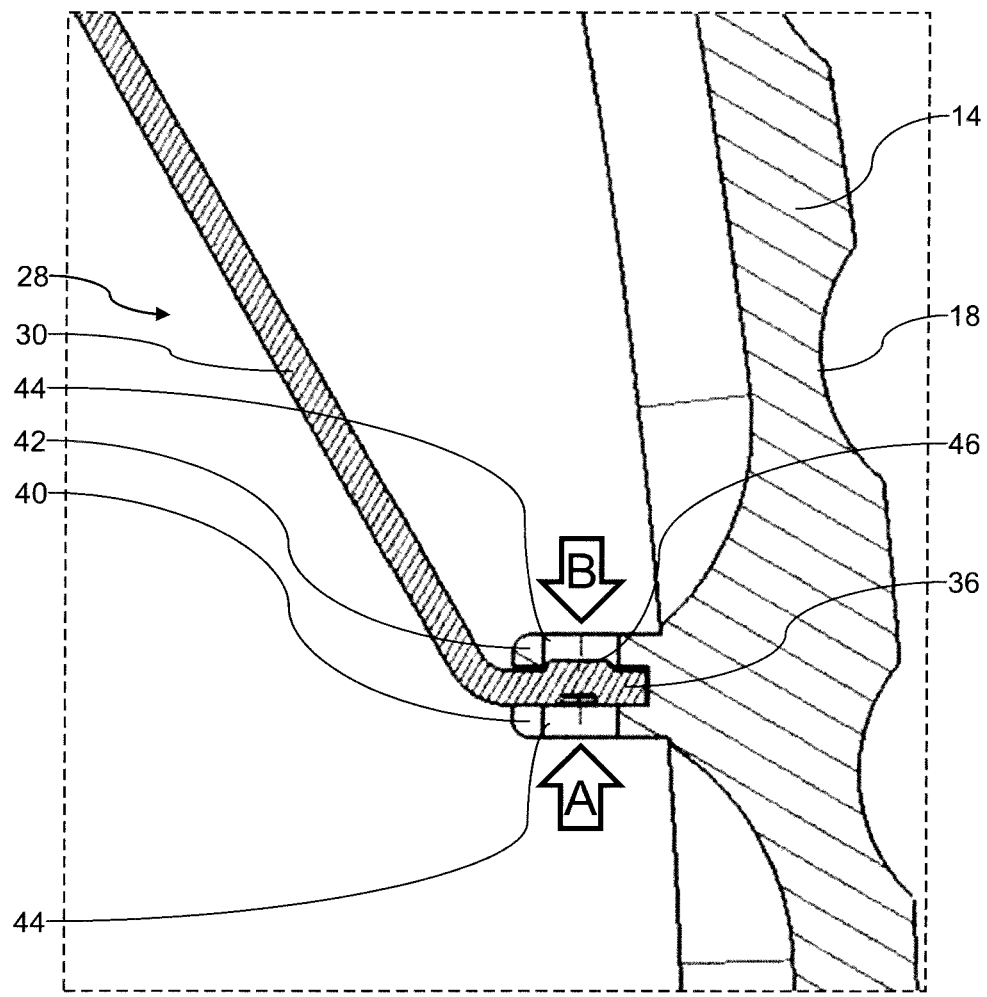
FIG. 2 shows a cross-sectional view of a catching of a spring element end with a handle element according to the invention as set forth in the first embodiment.

In order to catch the connecting portion 36 with the handle element 14 and, resp., in order to catch the connecting portion 38 with the handle element 16, the connecting portion 36 and, resp., 38 is clinched over the cutouts 44 as shown in FIG. 2. More exactly speaking, initially the connecting portion 36 and, resp., 38 is inserted between the connecting plates 40 and 42. Subsequently, a tool (not shown) is passed through the recess 44 of the connecting plate 40 and is pressed against the connecting portion 36 and, resp., 38 (cf. arrow A in FIG. 2) so that the connecting portion 36 and, resp., 38 is locally deformed and the clinching projection 46 brought about by the deformation projects into the cutout 44 of the connecting plate 42. Hence, the catching and, resp., the engagement of the spring element 28 with the handle element 14 and, resp., 16 is primarily achieved by catching or engaging the clinching projection 46 in the connecting plate 42. In other words, the clinching projection 46 forms an undercut according to the invention which is positively connected to the handle element 14 via the connecting plates 40 and 42 thereof.

In order to release the catching or engagement of the spring element 28 in the handle element 14 and, resp., 16, the tool (not shown) merely has to be passed through the cutout 44 of the connecting plate 42 and has to be pressed against the clinching projection 46 (see arrow B in FIG. 2) so that the connecting portion 36 and, resp., 38 is locally formed back, thus causing the clinching projection 46 to be leveled and to stop projecting into the cutout 44 of the connecting plate 42. Consequently, the release of the catching or engagement of the spring element 28 in the handle element 14 or 16 can be achieved only by destroying the clinching projection 46. Non-destructive release is not possible.

The relative position of the handle elements 14 and 16 in which the spring element 28 caught or engaged in the handle elements 14 and, resp., 16 is not tensioned, hereinafter will be referred to as initial position. In the initial position the connecting plate 40 of the handle element 14 is aligned with the connecting plate 40 of the handle element 16. Accordingly, the connecting plate 42 of the handle element 14 is aligned with the connecting plate 42 of the handle element 16.

By the fact that the clearance between the connecting plates 40 and 42 of the handle element 14 and, resp., 16 is freed even in the direction normal to the swivel plane of the handle elements 14 and 16, the spring element 28 can be inserted for being mounted also laterally, i.e. in the direction normal to the swivel plane of the handle elements 14 and 16, with its connecting portions 36 and 38 between the connecting plates 40 and 42 of the handle elements 14 and 16.

In the above-described first embodiment, the recesses 44 are configured in such a way and the respective connecting portion 36 and, resp., 38 is inserted between the respective connecting plates 40 and 42 so far that, after reshaping the connecting portion 36 and, resp., 38, around the clinching projection 46 furthermore areas of the connecting portion 36 and, resp., 38 are caught between the respective connecting plates 40 and 42.

The second embodiment of the invention shown in FIGS. 3A and 3B differs from the first embodiment to the effect that a cutout 144 in a connecting plate 142 is formed to be so large that the free end of a connecting portion 136 of a spring element 128 can completely immerse into the cutout 144 after reshaping the spring element 128. In the second embodiment, thus no clinching projection 46 but a canting 148 is formed by reshaping. The catching or engagement of the spring element 128 is achieved by beading rather than by clinching.

In the third embodiment of the invention shown in FIGS. 4A and 4B, too, the catching or engagement of a spring element 228 in a handle element 214 is achieved by means of a beaded canting 248 at a connecting portion 236. However, the handle element 214 includes only one connecting plate 240. The connecting plate 240 includes at its free end two projections 250 extending substantially in parallel to the handle element 214 which at their free ends have through-holes into which a pin 252 can be inserted with press fit so that the pin 252 together with the projections 250 and the connecting plate 240 forms an eyelet 244 for catching or engagement with the canting 248. The gap between the projections 250 extends in parallel to the direction of extension of the handle element 214 and, resp., the pin 252 extends in parallel to the swivel axis of a hinge of the hand-held instrument according to the third embodiment (cf. hinge 8 in the first embodiment).

In contrast to the first two embodiments, in the third embodiment of the invention the spring element 228 is reshaped before mounting with the handle element 214. For mounting, the spring element 228 is moved with its canting 248 between the projections 250 onto the connecting plate 240 and, resp., is put against the connecting plate 240 so that a space restricted by the canting 248 is aligned with through-holes at the ends of the projections 250. By subsequent introduction of the pin 252 into the through-holes, the canted end of the spring element 228 is caught, thus bringing about the catching or engagement of the spring element 228 with the handle element 214.

In the fourth embodiment of the invention shown in FIGS. 5A to 5D, too, a spring element 328 is reshaped already before mounting. As in the second and third embodiments, also in the fourth embodiment the catching or engagement of a spring element 328 with a handle element 314 is achieved by means of beading. However, a free end of a connecting portion 336 is not only canted but completely folded over and thus includes a fold 354. The handle element 314 includes two projections 356 extending in the direction of another handle element 328 (shown in FIGS. 5C and 5D). As in the third embodiment, the clearance between the projections 356 extends in parallel to the direction of extension of the handle element 314. In order to connect the spring element 328 to the handle element 314, the projections 356 at their free ends include through-holes into which a pin 352 can be inserted with press-fit such that the pin 352 together with the projections 356 and the handle element 328 forms an eyelet 344 for catching or engagement with the fold 354. For mounting, the spring element 328 is moved with its fold 354 between the projections 356 onto the handle element 314 and, resp., is put against the handle element such that a space restricted by the fold 354 is aligned with the through-holes at the ends of the projections 356. By subsequent introduction of the pin 352 the folded-over end of the spring element 328 is caught, thus bringing about the catching or engagement of the spring element 328 with the handle element 314. Since the handle element 314 includes no connecting plates, the connecting portion 336 caught or engaged with the pin 352 can be swiveled about the pin 352 in the mounted state of the spring element 328.

Using the example of the fourth embodiment, it is illustrated that on a hand-held instrument according to the invention merely one of two spring element ends must be caught or engaged with a handle element in a way according to the invention. As shown in FIGS. 5C and 5D, a connecting portion 338 of the spring element 328 can be canted only such that it can merely be inserted into a seat 358 formed at the handle element 316 and in the following also referred to as spring element end seat rather than be caught with the handle element 316.

In FIGS. 6A to 6C, a fifth embodiment of the invention is shown. A connecting portion 436 of a spring leaf-shaped spring element 428 includes two perforations 460 which are arranged such that a T-shaped end portion 462 is formed at the spring element 428. In other words, the connecting portion 436 has two projections which are arranged such that the T-shaped end portion 462 is formed. The cross-beam 463 of the T-shaped end portion 462 serves as swivel axis for the spring element 428 in the mounted state. The handle element 414 includes, on the side facing the other handle element (not shown), two projections 456 extending toward the other handle element which extend in parallel to the extension direction of the handle element 414. At their respective free ends, each of the projections 456 includes a bearing eye 464 having a slit 466 that extends to the edge of the respective projection 456. Cross-beam 463 defines a first thickness 463A (see FIG. 6A) and a second thickness 463B (see FIG. 6B) perpendicular to the first thickness. Second thickness 463B is larger than first thickness 463A. The width 466A of the slit 466 (see FIG. 6C) is only insignificantly larger than first thickness 463A of the spring element 428, but smaller than second thickness 463B.

For catching the spring element 428 according to the fifth embodiment with the corresponding handle element 414, the cross-beam 463 of the T-shaped end portion 462 is inserted into the bearing eye 464 through the slit 466. During said insertion, one leg 430 of the spring element 428 necessarily has to be aligned in parallel to the slit 466 (cf. indicated mounting position C in FIG. 6C). This has to be done equally with the other handle element (not shown) to mount the spring element 428. In order to finally catch and, resp., engage the spring element 428 with the handle elements, the spring element has to be reshaped in such way that the leg 430 thereof and the other leg (not shown) extend toward the hinge (not shown) of the hand-held instrument according to the fifth embodiment and the cross-beam 463 of the T-shaped end portion 462 is rotated so that it cannot be moved through the slit 466 anymore (see initial position D in FIG. 6C). The situation of the cross-beam 463 being caught in the bearing eyes 464 is retained until the legs of the spring element 428 are not swiveled deliberately into the mounting position C. Especially in a typical swivel range E (see FIG. 6C) in which the legs of the spring element 428 are moving during use of the hand-held instrument according to the fifth embodiment, the end portions of the spring element 428 remain caught in the bearing eyes of the handle elements. Of preference, the spring element 428 is configured so that each position within the swivel range E is more stable than the mounting position C. In order to nevertheless enable an as simple mounting as possible, the spring element 428 may be in the form of a clicker in which the mounting position C represents at least a metastable position of the spring element 428.

The embodiments of the medical hand-held instrument according to the invention shown in FIGS. 1 to 6C and described in the foregoing illustrate merely five possible implementations.

The invention claimed is:
1. A medical hand-held instrument comprising:
   a first handle element and a second handle element that swivel relative to each other; and
   a spring element comprising a bent leaf spring having a first spring element end and a second spring element end,
   the first handle element comprising a first pair of connecting plates that extend parallel with one another toward the second handle element and form a first gap between said first pair of connecting plates,
   the second handle element comprising a second pair of connecting plates that extend parallel with one another toward the second handle element and form a second gap between said second pair of connecting plates,
   the first pair of connecting plates defining at least one first aperture extending within one of the first pair of connecting plates, the at least one first aperture extending in communication with the first gap,
   the second pair of connecting plates defining at least one second aperture extending within one of the second pair of connecting plates, the at least one second aperture extending in communication with the second gap,
   the first spring element end comprising at least one first projection that is received in the at least one first aperture to connect the first spring element end to the first handle element, and
   the second spring element end comprising at least one second projection that is received in the at least one second aperture to connect the second spring element end to the second handle element, the second spring element end being fixed relative to the second handle element,
   the at least one first aperture comprising a cutout defined in each of the first pair of connecting plates,
   the at least one first projection being received in both of the cutouts and comprising two projections forming a T-shaped end, and at least one of the first pair of connecting plates comprising a slit defining a width and extending to an edge of said at least one of the first pair of connecting plates, the slit extending in communication with the at least one first aperture as well as the first gap and extending transversely to a cross-beam of the T-shaped end.

2. The medical hand-held instrument according to claim 1, wherein the width of the slit is only insignificantly larger than a thickness of the spring element.

3. The medical hand-held instrument according to claim 1, wherein the spring element further comprises a first leg, a second leg, a curved portion which interconnects the first leg and the second leg, and
the first spring element end is at a free end of the first leg and the second spring element end is at a free end of the second leg.

4. The medical hand-held instrument according to claim 3, wherein the first leg, the second leg, the curved portion, the first spring element end and the second spring element end are formed integrally.

5. The medical hand-held instrument according to claim 1, wherein the spring element is substantially U or V shaped.

6. The medical hand-held instrument according to claim 1, wherein the spring element comprises a clicker.

7. The medical hand-held instrument according to claim 1, wherein the cross-beam of the T-shaped end has a rectangular cross section defined by a first thickness and a second thickness perpendicular to the first thickness, the second thickness larger than the first thickness.

8. The medical hand-held instrument according to claim 7, wherein the width of the slit is larger than the first thickness of the cross-beam to allow insertion of the T-shaped end through the slit and into the first gap and first aperture when the cross-beam is in a first orientation.

9. The medical hand-held instrument according to claim 8, wherein the width of the slit is smaller than the second thickness of the cross-beam so that, after inserting the T-shaped end into the slit and into the first gap and first aperture, and after rotating the T-shaped end to a second orientation different from the first orientation, the cross-beam is caught in the first gap and first aperture and prevented from exiting the first gap and the first aperture through the slit.

10. A medical hand-held instrument comprising:
a first handle element and a second handle element that swivel relative to each other; and
a spring element comprising a bent leaf spring having a first spring element end and a second spring element end,
the first handle element comprising a first pair of connecting plates that extend parallel with one another toward the second handle element and form a first gap between said first pair of connecting plates,
the second handle element comprising a second pair of connecting plates that extend parallel with one another toward the second handle element and form a second gap between said second pair of connecting plates,
the first pair of connecting plates defining at least one first aperture extending within one of the first pair of connecting plates, the at least one first aperture extending in communication with the first gap,
the second pair of connecting plates defining at least one second aperture extending within one of the second pair of connecting plates, the at least one second aperture extending in communication with the second gap,
the first spring element end comprising at least one first projection that is received in the at least one first aperture to connect the first spring element end to the first handle element,
the second spring element end comprising at least one second projection that is received in the at least one second aperture to connect the second spring element end to the second handle element,
the at least one first aperture comprising a cutout defined in each of the first pair of connecting plates,
the at least one first projection being received in both of the cutouts and comprising two projections forming a first T-shaped end,
at least one of the first pair of connecting plates comprising a first slit defining a first width and extending to an edge of said at least one of the first pair of connecting plates, the first slit extending in communication with the at least one first aperture as well as the first gap and extending transversely to a cross-beam of the first T-shaped end,
the at least one second aperture comprising a cutout defined in each of the second pair of connecting plates,
the at least one second projection being received in both of the cutouts and comprising two projections forming a second T-shaped end, and
at least one of the second pair of connecting plates comprising a second slit defining a second width and extending to an edge of said at least one of the second pair of connecting plates, the second slit extending in communication with the at least one second aperture as well as the second gap and extending transversely to a cross-beam of the second T- shaped end.

11. The medical hand-held instrument according to claim 10, wherein
the first width of the first slit of the first pair of connecting plates is only insignificantly larger than a thickness of the spring element, and
the second width of the second slit of the second pair of connecting plates is only insignificantly larger than the thickness of the spring element.

12. The medical hand-held instrument according to claim 10, wherein the cross-beams of the first T-shaped end and the second T-shaped end each have a rectangular cross section defined by a first thickness and a second thickness perpendicular to the first thickness, the second thickness larger than the first thickness.

13. The medical hand-held instrument according to claim 12, wherein the first width of the first slit and the second width of the second slit are each larger than the first thicknesses of the cross-beams to allow insertion of the first T-shaped end and the second T-shaped end through the first slit and the second slit, respectively, when each cross-beam is in a first orientation.

14. The medical hand-held instrument according to claim 13, wherein the first width of the first slit and the second width of the second slit are each smaller than the second thicknesses of the cross-beams so that, after inserting the first T-shaped end and the second T-shaped end into the first slit and the second slit, respectively, and after rotating each of the cross-beams to a second orientation different from the first orientation, the cross-beam of the first T-shaped end is caught in the first aperture and prevented from exiting the first aperture through the first slit, and the cross-beam of the second T-shaped end is caught in the second aperture and prevented from exiting the second aperture through the second slit.

* * * * *